United States Patent [19]

Costello et al.

[11] Patent Number: 5,035,841
[45] Date of Patent: Jul. 30, 1991

[54] TRIBLOCK AMIDE FLUOROSURFACTANTS

[75] Inventors: Christine A. Costello, Easton; John B. Dickenson, Fogelsville, both of Pa.

[73] Assignee: Air Products and Chemicals, Inc., Allentown, Pa.

[21] Appl. No.: 346,106

[22] Filed: May 2, 1989

[51] Int. Cl.$^5$ .............................. C09F 5/00; C09F 7/00
[52] U.S. Cl. .................................................. 260/404.5
[58] Field of Search ................................ 260/404.5 F

[56] References Cited

U.S. PATENT DOCUMENTS

| | | | |
|---|---|---|---|
| 3,472,894 | 10/1968 | Bartlett | 260/561 |
| 3,547,995 | 12/1970 | Bartlett | 260/561 |
| 3,576,017 | 4/1971 | Sweeney et al. | 200/404.5 F |
| 3,600,415 | 8/1971 | Sweeney | 260/404.5 |
| 3,621,059 | 11/1971 | Bartlett | 260/561 |
| 3,828,085 | 8/1974 | Price et al. | 260/404.5 |
| 4,079,084 | 3/1978 | Houghton | 260/615 |
| 4,171,282 | 10/1979 | Mueller | 252/356 |

OTHER PUBLICATIONS

J. Afzal, B. M. Fung, E. A. O'Rear; "Synthesis of Perfluoroalkyl N-Polyethoxylated Amides"; *Journal of Fluorine Chemistry*; 34, (1987), 385-393.

Primary Examiner—Jose G. Dees
Assistant Examiner—Deborah D. Carr
Attorney, Agent, or Firm—Michael Leach; James C. Simmons; William F. Marsh

[57] ABSTRACT

A compound of the formula

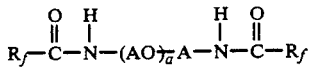

Where
$R_f$ is a perfluorinated $C_2$-$C_{20}$ hydrocarbyl group,
A is a $C_2$-$C_4$ alkylene group, and
a is from 1 to 1000.

These triblock amide perfluoro compounds are useful as surfactants.

22 Claims, No Drawings

TRIBLOCK AMIDE FLUOROSURFACTANTS

TECHNICAL FIELD

The present invention relates to fluorosurfactants and, more particularly, relates to nonionic fluorosurfactants containing polymerized alkylene oxide units.

BACKGROUND OF THE INVENTION

Surfactants are materials used to address problems in areas relating to altering conditions at interfaces. For example, surfactants are used as detergents, emulsifiers, wetting agents, anti-static agents and the like, where changes in liquid-liquid or liquid-air interfaces are needed. Also, surfactants may be used when conditions at solid-liquid interfaces require alteration, such as reduction of friction at solid surfaces. A specific use of surfactants involves their ability to lower critical surface tensions of liquids, promoting better "wetting" of surfaces.

One effective solution to the problem of reducing altering conditions at interfaces is through the use of fluorosurfactants. These compounds fall into two major classes: ionic and nonionic. Ionic fluorosurfactants are characterized by a long chain perfluorocarbon lyophobic tail and a polar (cationic or anionic) head. These types of compounds usually form micelles when they are present in systems above their critical micelle concentration (CMC).

As the name implies the molecules of the nonionic fluorosurfactants do not contain an ionic head. The lyophilic end of the molecule results from a water soluble polymer or oligomer block of an alkylene oxide, for example, ethylene oxide.

Fluorosurfactants may be used to stabilize aqueous emulsions of perfluorinated fluorinated hydrocarbons. These materials act as oxygen and carbon dioxide transport agents useful as blood substitutes in mammals.

U.S. Pat. No. 3,472,894 discloses perfluoroalkyl ether bis(hydroxyalkyl) amides of the formula $R_fO(C_3F_6O)_nCF(CF_3)CON(C_pH_{2p}OH)_2$ useful as surface active agents.

U.S. Pat. No. 3,547,995 discloses perfluoroalkyl ether amidoamine oxides of the formula $R_fO(C_3F_6O)_nCF(CF(CF_3)CON(R')Q$ in which Q is selected from certain radicals containing an amine oxide group useful as surface active agents.

U.S. Pat. No. 3,600,415 discloses fluoronated amides useful as oil-repelling agents having the structural formula $$R_f-\overset{O}{\underset{\|}{C}}-\overset{Y}{\underset{|}{N}}-(R-N)_q-RQ$$

where $R_f$ is a fluorine-containing isoalkoxyalkyl group and R is a divalent alkylene bridging group.

U.S. Pat. No. 3,621,059 discloses amides derived from hexafluoropropylene oxide polymer acids and polyalkylene oxide having the formula

useful as surfactants and emulsifying agents.

U.S. Pat. No. 3,828,085 discloses amidoamine oxides of the formula

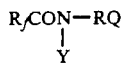

where $R_f$ is a perfluoroalkyl group or a polyfluoroisoalkoxyalkyl group useful as surface active agents.

U.S. Pat. No. 4,079,084 discloses fluorocarbon surfactants containing a nonionic hydrophilic chain (preferably an oxyethylene chain) and at least two terminal perfluorocarbon groups of at least three carbon atoms, preferably branched perfluorocarbon groups derived from an oligomer of tetrafluoroethylene.

U.S. Pat. No. 4,171,282 discloses perfluoroalkylthio-substituted half esters and amides of succinic acid having the formula

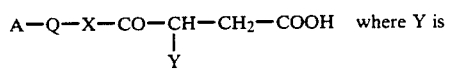

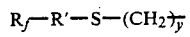

where Y is $R_f-R'-S-(CH_2)_y$ useful as surfactants. J. Afzal, et al., J. of Fluorine Chem., 34 (1987) 385–393 discloses monodisperse perfluoroalkyl N-polyethoxylated amides $C_nF_{2n+1}CONH(CH_2CH_2O)_mH$ as potential nonionic fluorinated surfactants.

SUMMARY OF THE INVENTION

The present invention provides triblock amide fluorosurfactants of the formula:

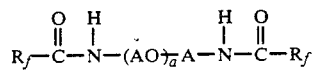

where
$R_f$ is a perfluorinated $C_2-C_{20}$ hydrocarbyl group,
A is a $C_2-C_4$ alkylene group, and
a is an integer from 1 to 1000.

Compounds of the above formula may be added to a liquid with high surface tension to lower the surface tension or to enhance wetting of a solid by the liquid.

As an advantage the solubility of a fluorosurfactant of the invention can be controlled by the length of the lyophilic portion of the molecule.

DETAILED DESCRIPTION OF THE INVENTION

The present invention involves the synthesis of triblock amide fluorosurfactants from perfluoro acid chlorides and various poly(alkyleneoxy) diamines. The triblock amide fluorosurfactants are represented by the following general formula:

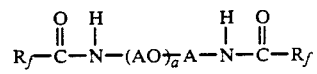

where
$R_f$ is a perfluorinated $C_2-C_{20}$ hydrocarbyl group, preferably a alkyl group,
A is a $C_2-C_4$ alkylene group, preferably ethylene and/or propylene, and a is an integer from 1 to 1000, preferably 1 to 30 and most preferably 1 to 12.

The lyophobic portion of the molecule is represented by the $R_f$ group which may, for example, be $$(CF_3)_2CF-(CF_2)_p-$$

where p is an integer from 0 to 17, or preferably the fluorinated straight chain alkyl $$F-(CF_2)_n-$$

where n is an integer from 2 to 20. It is preferred that p and n range from 2 to 10.

The lyophilic portion of the molecule is a poly(alkyleneoxy)-type structure. This moiety may comprise repeating units of a single $C_2$-$C_4$ alkyleneoxy group or any combination of such alkyleneoxy groups, for example blocks of ethyleneoxy and propyleneoxy groups.

The fluorosurfactants of the invention are synthesized by condensing a perfluoro acid chloride of the formula:

$$R_f-\overset{\overset{O}{\|}}{C}-Cl$$

with an alkylene glycol diamine of the formula:

$$H_2N-(AO)_a-A-NH_2$$

Where $R_f$, A and a are as defined above.

Two molar equivalents of the acid chloride are reacted per mole of diamine in the presence of an acid scavenger, such as pyridine or triethylamine. Organic solvents such as tetrahydrofuran and diethyl ether can be used.

The perfluoro acid chlorides can be prepared according to the procedures in U.S. Pat. No. 2,559,630 and are commercially available from PCR and Alfa. Procedures for preparing the diamines can be found in U.S. Pat. No. 3,236,895 and suitable diamines for use in the preparation of the fluorosurfactants can be purchased under the trademark Jeffamine ® from Texaco Chemical Corporation.

The Jeffamine diamine used can be any of those which are commercially available. The higher molecular weight diamines, however, are polydisperse as a result of the procedure by which they were synthesized. These diamine products will yield polydisperse fluorosurfactants. The lower molecular weight diamine products, for example Jeffamine 148 and 192 diamines, will yield monodisperse surfactants.

Although the amide fluorosurfactants in the examples were synthesized from the acid chloride, they can also be synthesized from the corresponding carboxylic acids and esters, using well known, suitable conditions for reacting an acid or ester with an amine to yield an amide.

EXAMPLE 1

Jeffamine ® EDR 148 diamine [0.5 ml; $3.5 \times 10^{-3}$ mole] and 1.0 ml ($8.0 \times 10^{-3}$ mole) pyridine were dissolved in 5 ml tetrahydrofuran (THF) which was distilled from calcium hydride. This solution was added dropwise under nitrogen to a solution of 5 ml perfluorooctanoyl chloride in 5 ml THF; a white precipitate immediately formed which was assumed to be pyridinium hydrochloride since it was water soluble. The reaction proceeded at room temperature for 0.5 hour. At the end of the reaction period, the white precipitate was filtered off using a 2.5 micron filter paper. Methylene chloride (105 ml) was added to the filtrate yielding more water soluble white precipitate which was filtered off. Methylene chloride (150 ml) was added again; this time there was no precipitate. The filtrate was rotavapped to dryness. A white solid powder (2.7 g) was isolated whose NMR and IR spectra were consistent with the following structure:

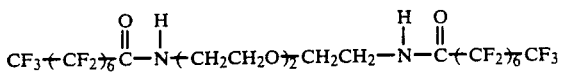

EXAMPLE 2

The procedure of Example 1 was followed using Jeffamine EDR 192 diamine and 3 ml perfluorooctanoyl chloride. The product was a yellow oil; removal of pyridinium hydrochloride was effected by dissolution of the amide product in diethyl ether and subsequent extraction with water. The product yield was 1.6 g. The IR and NMR spectra were consistent with the following structure:

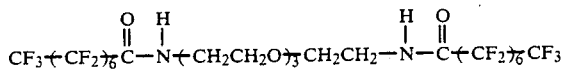

EXAMPLE 3

A solution of 17.2 g of Jeffamine ED 600 diamine and 4.64 ml ($5.8 \times 10^{-2}$ mole) pyridine was added to a solution of 24.91 g ($5.8 \times 10^{-2}$ mole) perfluorooctanoyl chloride in 75 ml diethyl ether. The reaction proceeded for 2.5 hours at room temperature. A white precipitate immediately formed. At the end of the reaction period, 200 ml additional diethyl ether was added and the solution filtered on a 2.5 micron filter. The filtrate was rotavapped to dryness. NMR of the product indicated trace pyridinium hydrochloride, so the product was dissolved in a 5/1/94 v/v solution of methanol/N-H$_4$OH/chloroform and filtered through silica gel. The filtrate was rotavapped to dryness; NMR and IR spectra were consistent with the following product:

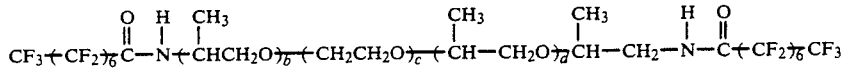

where
c=8.5
b+d=2.5

EXAMPLE 4

The ability of the fluorosurfactant to lower the surface tension of liquids when added in relatively low concentrations is demonstrated by this Example. The fluorosurfactant of Example 3 was added to a commercial solvent in various levels and compared to similar data on commercially available surfactants as shown in Table 1.

TABLE 1

| Solvent | Dynes/cm | Additive | Dynes/cm 0.1% Additive | 1.0% Additive |
|---|---|---|---|---|
| Aromatic 100 | 43.2 | Fluorosurfactant | 34.0 | 29.0 |
| Aromatic 100 | 43.2 | Surfynol-440 | 32.5 | 29.7 |
| Aromatic 100 | 43.2 | Surfynol-465 | 28.1 | 29.8 |
| Aromatic 100 | 43.2 | Surfynol-104 | 35.4 | 30.0 |
| Aromatic 100 | 43.2 | Wacker - Al | 30.3 | 27.8 |
| Aromatic 100 | 43.2 | Wacker - 051 | 30.2 | 26.5 |
| Aromatic 100 | 43.2 | Byk-320 | 33.9 | 30.0 |
| Aromatic 150 | 40.6 | Fluorosurfactant | 38.8 | 27.4 |
| Aromatic 150 | 40.6 | Surfynol-440 | 40.2 | 40.0 |
| Aromatic 150 | 40.6 | Surfynol-465 | 39.1 | 37.8 |
| Aromatic 150 | 40.6 | Surfynol-104 | 40.1 | 37.4 |
| Aromatic 150 | 40.6 | Wacker - Al | 26.5 | 24.5 |
| Aromatic 150 | 40.6 | Wacker - 051 | 31.0 | 28.6 |
| Aromatic 150 | 40.6 | Byk 320 | 36.3 | 35.8 |

STATEMENT OF INDUSTRIAL APPLICATION

The invention provides triblock amide perfluoro materials useful as surfactants.

We claim:

1. A compound of the formula:

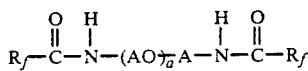

where $R_f$ is a perfluorinated $C_2$-$C_{20}$ hydrocarbyl group, A is a $C_2$-$C_4$ alkylene group, and a is an integer from 1 to 1000.

2. The compound of claim 1 in which $R_f$ is a perfluorinated alkyl group.

3. The compound of claim 1 in which $R_f$ is a perfluorinated $C_2$-$C_{10}$ alkyl group.

4. The compound of claim 1 in which $R_f$ is $(CF_3)_2CF\!-\!(CF_2)_p\!-$ where p is an integer from 0 to 17.

5. The compound of claim 4 in which p is 2 to 10.

6. The compound of claim 1 in which $R_f$ is $F\!-\!(CF_2)_n\!-$ where n is an integer from 2 to 20.

7. The compound of claim 6 in which n is 2 to 10.

8. The compound of claim 1 in which A is ethylene.

9. The compound of claim 1 in which A is ethylene and/or propylene.

10. The compound of claim 1 in which a is from 1 to 30.

11. The compound of claim 1 in which a is from 1 to 12.

12. A compound of the formula

where
A is ethylene and/or propylene,
a is 1 to 30, and
n is 2 to 20.

13. The compound of claim 12 in which n is from 2 to 10.

14. The compound of claim 12 in which n is 7.

15. The compound of claim 12 in which A is ethylene.

16. The compound of claim 15 in which a is 1 to 12.

17. The compound of claim 15 in which a is 2.

18. The compound of claim 15 in which a is 3.

19. The compound of claim 12 in which $-(AO)_a A-$ is

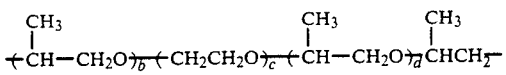

where
c = 8.5
b + d = 2.5

20. The compound of claim 19 in which n is 2 to 10.

21. The compound of claim 19 in which n is 7.

22. A compound of the formula

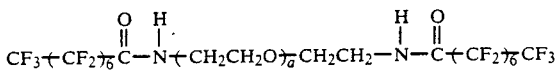

where a is 2 or 3.

* * * * *

UNITED STATES PATENT AND TRADEMARK OFFICE
CERTIFICATE OF CORRECTION

PATENT NO. : 5,035,941
DATED : July 30, 1991
INVENTOR(S) : William A. Blackburn

It is certified that error appears in the above-identified patent and that said Letters Patent is hereby corrected as shown below:

Column 10, line 17, insert "to" after --order--.

Column 12, line 6, correct "weigh" to read --weight--.

Column 12, line 16, insert "1" after --claim--.

Signed and Sealed this

Twenty-second Day of December, 1992

Attest:

DOUGLAS B. COMER

*Attesting Officer*      *Acting Commissioner of Patents and Trademarks*